United States Patent [19]
Valenti

[11] Patent Number: 5,813,975
[45] Date of Patent: Sep. 29, 1998

[54] DOUBLE LAYER DYNAMIC PROSTHESIS FOR SURGICAL TREATMENT OF THE INGUINAL HERNIA

[76] Inventor: Gabriele Valenti, Via Nicola Fabrizi, 8, I-00153 Roma, Italy

[21] Appl. No.: 669,471
[22] PCT Filed: Nov. 7, 1995
[86] PCT No.: PCT/IT95/00179
  § 371 Date: Jul. 8, 1996
  § 102(e) Date: Jul. 8, 1996
[87] PCT Pub. No.: WO96/14805
  PCT Pub. Date: May 23, 1996

[30] Foreign Application Priority Data

Nov. 9, 1994 [IT] Italy .............................. RM94A0730

[51] Int. Cl.$^6$ ....................................... A61F 2/00
[52] U.S. Cl. .............................................. 600/37
[58] Field of Search ................ 623/11, 14, 15, 623/13; 606/151, 152, 153, 154, 155, 156; 600/37

[56] References Cited

U.S. PATENT DOCUMENTS

| | | | |
|---|---|---|---|
| 4,204,282 | 5/1980 | Bolt | 623/14 |
| 4,769,038 | 9/1988 | Bendavid et al. | 623/13 |
| 4,786,276 | 11/1988 | Haber | 623/14 |
| 5,176,693 | 1/1993 | Wilk et al. | 606/151 |
| 5,433,996 | 7/1995 | Kranzler et al. | 623/14 |
| 5,507,811 | 4/1996 | Koike et al. | 606/151 |
| 5,593,441 | 1/1997 | Lichtenstein et al. | 606/151 |

FOREIGN PATENT DOCUMENTS 0614650  9/1994  European Pat. Off. .................. 623/14

*Primary Examiner*—Debra S. Brittingham
*Attorney, Agent, or Firm*—Browdy and Neimark

[57] ABSTRACT

The present invention relates to a double layer prothesis that is applied to every patient suffering from inguinal hernia. The two lower and upper layers of this dynamic prosthesis can move independently one from the other, since each of said two layers is fixed only on a side facing the side of the other layer. All this avoids, during muscular movements, (deambulation, cough efforts and so on), the formation of some traction and/or torsion points, frequently responsible for immediate post-operative and/or long term troubles and pains. The lower layer creates a new internal inguinal orifice and exercises a "sling" action on the spermatic cord. Said cord takes a "S" shape crossing the double prosthetic layer. The combination of the "sling" with the "S" shape of the cord prevents relapsing external oblique hernias.

5 Claims, 3 Drawing Sheets

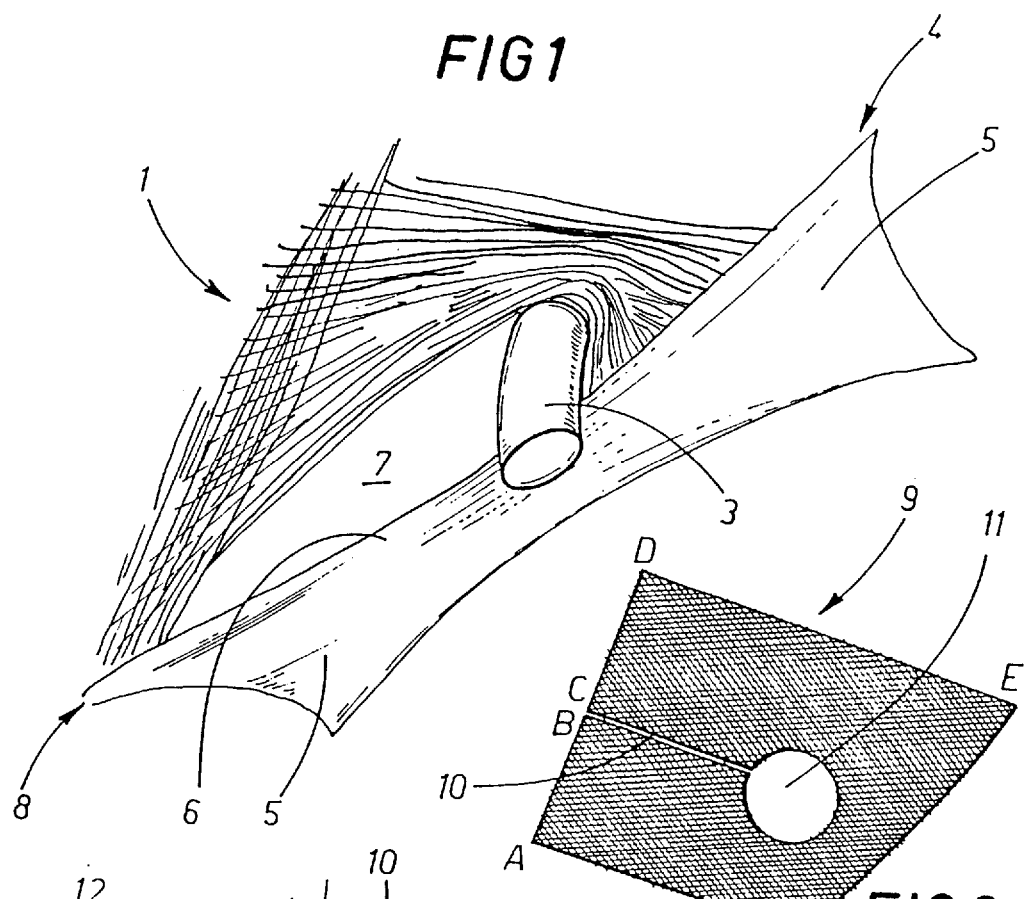
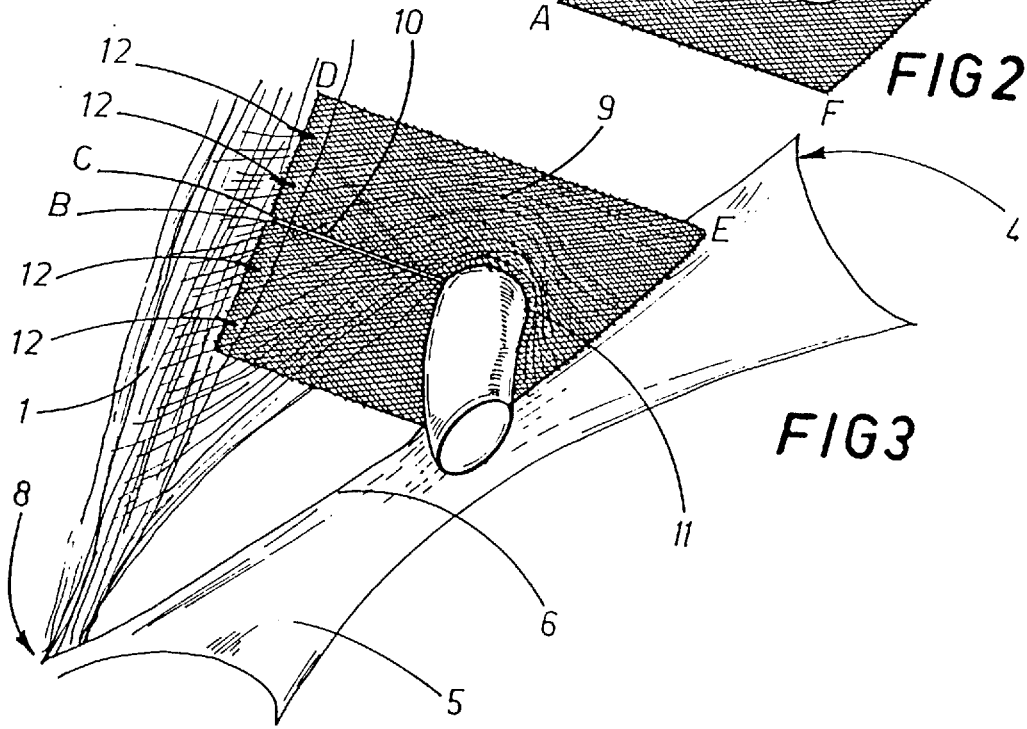

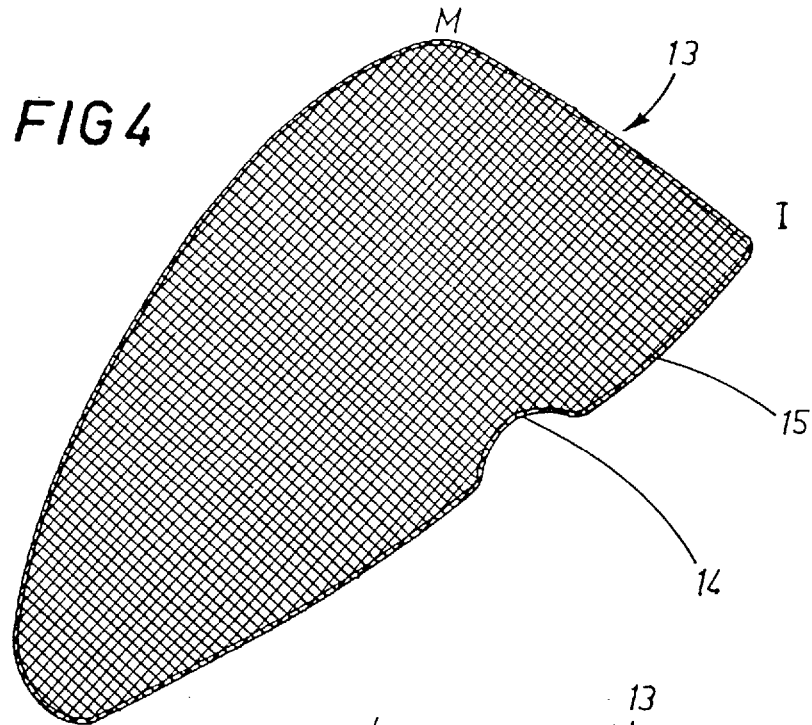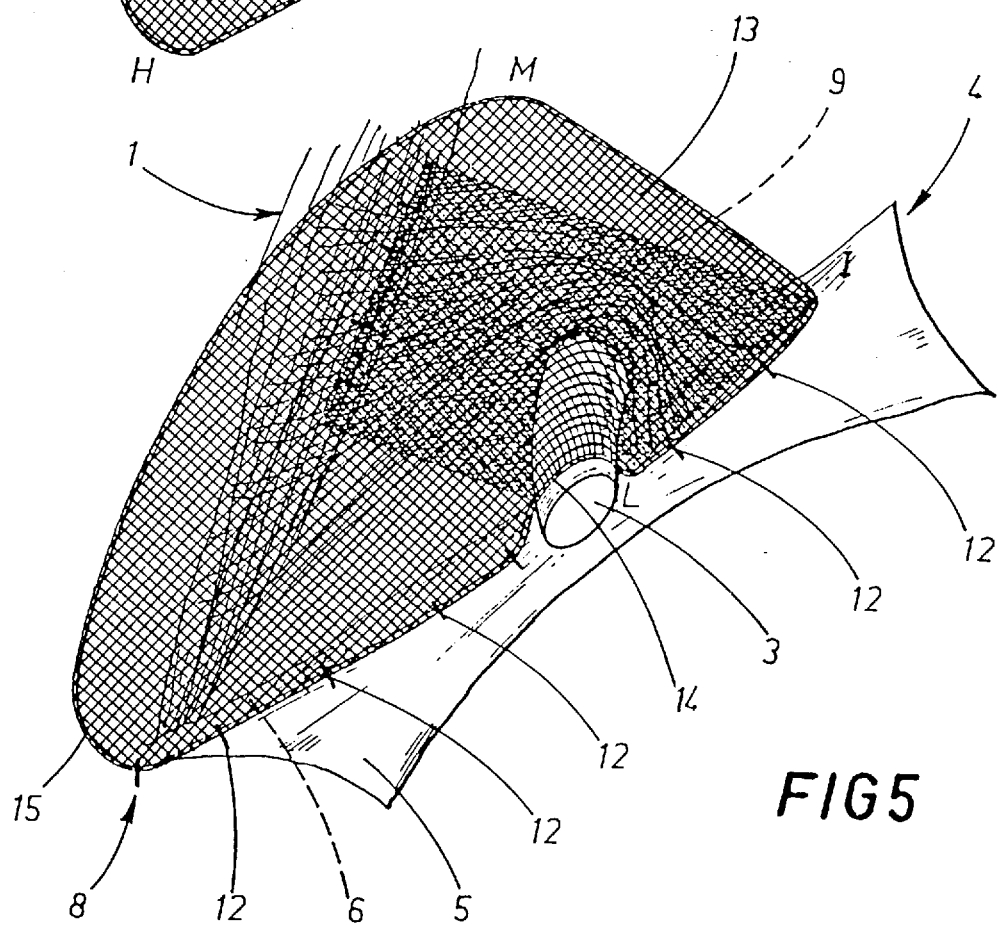

DOUBLE LAYER DYNAMIC PROSTHESIS FOR SURGICAL TREATMENT OF THE INGUINAL HERNIA

FIELD OF THE INVENTION

The invention relates to a prosthesis for inguinal hernia treatment of the type made with one thin layer of prosthesic material, which frequently includes mesh.

REVIEW OF THE RELATED TECHNOLOGY

The dynamic prosthesis is a prosthetic set constituted by two layers which may be reabsorbable or mixed materials which is applied to the floor of the inguinal canal as a treatment of an original or relapsing inguinal hernia. The two prosthetic layers are independent one from the other or are reciprocally fixed along a line or only in one point.

Examining surgical methodologies, performed presently all over the world, for applying a prosthesis for the inguinal hernia treatment, it is possible to determine two great groups of operations:

I) The ones that foresee the prosthesis sutured to the surrounding muscular aponeurotic structures, such as Lichtenstein's operation (free tension);

II) The ones that foresee the application of a sutureless prosthesis such as Gilbert's operation (sutureless).

The problems and limits of Lichtenstein's methodology are the excessive tension and bad distribution of the prosthesis which, being externally (that is along its periphery) sutured, isn't able to dynamically suit the modification of relationships among the anatomic structures of the inguinal canal. This produces pain that the patient frequently feels during the movements of the muscular-aponeurotic structures in the inguinal region (cough, effort, passage from the sitting to the upright position and so on).

Furthermore, the suture itself may cause possible traumas, whose consequences can be long term drawbacks or complications (lesions of vessels owing to stitches or traction, tissue lacerations, nerve lesions).

The surgeon who applies the above mentioned method, faces two problems: the first relating to the cutting out and defining of the shape of the prosthesis, which can be too large or too small; the second relating to the positioning of the prosthesis in the inguinal region; in fact, a too relaxed or stretched prosthesis or with tensions distributed in a faulty manner can be responsible for complications and persistent pains in the immediate post-operative period and/or in the long term.

In order to overcome the drawbacks caused by the operation with perimetric suture of the prosthesis (Liechtenstein's methodology), Gilbert and others thought to apply the mesh, without suturing it by previously including an underfascial "plug" in the internal inguinal orifice (a plug is a sort of prosthetic material cap of various shape and dimension inserted into the internal inguinal orifice in order to prevent an external oblique hernia).

This foreign body gives rise to several drawbacks, including for example:

perception of an inguinal tumefaction connected to sclerosis stimulated by the presence of the plug, which is felt by the patient with some discomfort;

displacement of the plug itself that could involve contact of the plug with the extraperitoneal organs (bladder, sigmoid colon, caecun) and cause possible bedsores on the viscera themselves;

difficulty in treating possible relapses in these conditions; and the great difficulties in treating postoperative suppuaration because of the presence of the underfascial plug that cannot be cleaned with a simple superficial dressing.

Furthermore, if we consider the hernia rate in the population, the constant use of properitoneal underfascial plug would cause a great number of patients to run the risk of prosthetic infection if an operation were necessary for a pelvic septic pathology (tumor of the colon, appendicitis, prostate, bladder).

If the plug tends to displace on the operating table, during short coughs, previously workers who themselves emphasise its application, are forced to fix it with suture stitches, thus denying the principle of "sutureless".

Since the only passage from the supine position to the upright position modifies the reciprocal relationships among the inguinal muscular aponeurotic structures, it should be taken into consideration that the sutureless mesh in the upper facial region, connected to the plug, can later displace and assume an incorrect position with respect to that performed by the surgeon during the operation.

In this way, the possibility of the rising of the prosthesis increases, mainly in the pubis region; such a complication is attested by the frequent relapses in this area even during the operations when the prosthesis is sutured.

Additionally, in the case of an unfixed prosthesis, the fibrousplastic reaction is delayed and hindered by the mesh mobility. As time passes, a cicatricial retraction additionally acts as a deforming element on the mesh itself.

Finally, if the application of a sutureless mesh is somehow justified in the case of an external oblique inguinal hernia not associated with internal inguinal ring widening, in the case of a direct hernia the same methodology is unsuitable since the yielding of the trasversalis layer is coupled with the yielding of the external inguinal ring and of the aponeurosis of the great oblique, said aponeurosis sometimes becoming a fibrous, sliding veil, which is unsuitable to support the prosthesis under abdominal pressure.

This explains why the same supporters of the free prosthesis application methodology, in some circumstances, apply suture stitches. Gilbert, in fact, limits such a method to cases where the internal inguinal orifice is not yielded and the floor of the inguinal canal is healthy.

It must also be added, generally, as there is no prepacked prosthesis adaptable to all kinds of hernia, that in many cases the prosthesis is cut out on the operating table by the surgeon himself in order to adapt it to several anatomic situations. Such a methodology may seem to be a positive fact, but on the contrary, it can cause several problems, listed hereunder:

in order to cut out the prosthesis, the surgeon has to interrupt the operation thus lengthening its duration;

the prosthesis cutting-cut and modelling performed by the surgeon on the spot may not be successful because of several environmental factors (stress, distraction or a lack of ability in "do it yourself");

the waste of material, due to the impossibility to re-use scraps of the modelled mesh, should not be undervalued considering the high number of operations of this kind carried out in most operating theatres.

It is stressed that there are too many elements of implicit improvisation during surgical procedures. Finally, the operation performed can be completely different to the one previously planned, because of a lack of standardised methodologies and because too many variables entrusted to the surgeon's discretion.

SUMMARY OF THE INVENTION

The aim of the present invention is to eliminate the above mentioned drawbacks and to use rationally the prosthesis during inguinal hernia operations.

A principal aim of the present invention is the creation of a prosthetic combination in order to avoid the tractions and tensions inherent to a prosthesis peripherally sutured, which allows a free and autonomous movement of the two prosthesis components. In this way the present invention maintains the advantageous characteristics of the prosthesis fixed along the whole periphery and overcomes the free prosthesis limits.

A further aim of the present invention is to make available a ready and suitable prosthesis to be easily applied in every patient and in every inguinal hernia according to a planned methodology which leaves little space for the surgeon's discretion and improvisation.

A still further aim of the present invention is to make possible a treatment of all inguinal hernias without penetrating a deep, underfascial area. Consequently, the operation is mostly performed on the surface and therefore less traumatic and invasive even in relation to possible suppuaration.

These and further aims of the present invention are achieved by a double layer dynamic prosthesis which, from a general point of view, is characterised in that it is constituted by a lower prosthetic layer and an upper prosthetic layer which is positioned on the lower prosthetic layer and both are independently mobile one from the other, being fixed with first and second suture stitches to the musculoaponeurotic structures of the inguinal canal, each prosthetic layer being fixed on only one of its sides which is opposite to that of the other layer; said two lower and upper prosthetic layers determining between themselves a "chicane" shape of the spermatic cord; said two lower and upper prosthetic layers carrying out a protection action of the inguinal canal in a coupled and complementary way on a variable area so as to adapt to the individual anatomic variations and to the modifications which come about in the patient during normal physical activity.

BRIEF DESCRIPTION OF THE DRAWING FIGURES

The present invention is described in more detail in the following description with the help of the attached drawings which represent a preferred embodiment in the form of a non-limiting example.

FIG. 1 shows the anatomic situation of the inguinal region.

FIG. 2 shows the lower prosthetic layer of the double layer prosthesis according to the present invention in a preferred but non-limiting embodiment.

FIG. 3 shows the lower prosthetic layer positioned shown FIG. 2.

FIG. 4 shows the upper prosthetic layer of the double layer prosthesis according to the present invention in a preferred but non-limiting embodiment.

FIG. 5 shows the prosthesis as a whole according to the present invention after the positioning of the upper layer.

Figure 6A:
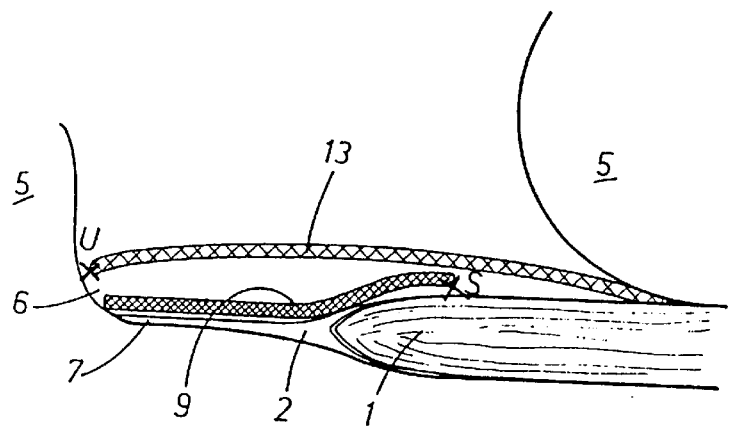
FIG. 6 shows three section drawings 6.1, 6.2, and 6.3 respectively.

6.1—the plane passing downstream the internal inguinal orifice;

6.2—the plane passing through the internal inguinal orifice;

6.3—the plane passing upstream the internal inguinal orifice.

DETAILED DESCRIPTION OF THE PREFERRED EMBODIMENT

According to the present invention, FIG. 1 schematically represents the anatomic situation of the inguinal region, once the hernia has been reduced, and in the figure the parts are denoted with the following numbers:

1 denotes the abdominus rectus muscle;

2 denotes the small oblique and transversalis muscles;

3 denotes the spermatic cord coming out from the internal inguinal orifice;

4 denotes the antero upper iliac spine;

5 denotes the external oblique muscle aponeurosis;

6 denotes the inguinal ligament;

7 denotes the floor of the inguinal canal covered by the trasversalis fascia;

8 denotes the pubic tubercle.

FIG. 2 shows a lower prosthetic layer 9 of the prosthesis according to the present invention, which is preferably trapezoidally shaped, in which the side A-D, corresponding to the medial border, shows an incision 10, at the end of which, an orifice 11 is modelled for the passage of the spermatic cord 3. The side E–F will be placed close to the inguinal ligament 6 without being sutured to it. Consequently, the side E–F, with respect to side A-D, is oblique, but hypothetically, any other shape can be equally valid, if it is capable of achieving the same effect.

The two medial offshoots A-B and C-D of the side A-D of the lower prosthetic layer 9 are destined to be fixed with suture stitches 12 to the sheath of the abdominus rectus muscle 1 (FIG. 3). This allows for movement of the mesh, making up the lower prosthetic layer 9, which movement is synchronous with the movements of the above mentioned muscle during cough or efforts of the abdominal wall and this motion causes no variation of the tension on the suture stitches. On the contrary, the "sling" action is emphasized on the spermatic cord 3, thus increasing the protection of the internal inguinal orifice.

FIG. 3 shows the lower layer 9 position of the dynamic prosthesis according to the present invention; the A-B and C-D offshoots are fixed with suture stitches 12 to the rectus muscle 1; the E–F side corresponds to the inguinal ligament 6 stretched between the pubis tubercle 8 and the entero upper iliac spine 4; the A-F side is found downstream the orifice 11. From the orifice 11 comes out the spermatic cord 3.

FIG. 4 shows an upper prosthetic layer 13 of the prosthesis according to the present invention in which one side H-I is destined to be fixed with first suture stitches 12 (FIG. 5) from the tubercle of the pubis 8 so as to largely pass the internal inguinal orifice according to an orientation overlapping that of the inguinal ligaments 6 even if such shape is not restrictive and non-limiting. The H-I side advantageously shows a semilunar incision 14, also in a non-limiting form which allows and facilitates the passage to the surface of the spermatic cord 3. This completes the S-shaped passage of the spermatic cord itself between the two lower 9 and upper 13 prosthetic layers.

The H-M medial side of the upper prosthetic layer 13 is destined to remain free and laid down on the abdominis rectus muscle sheath 1. The preferred rounded shape of the line H-M follows the line corresponding to the fusion of the external oblique aponeurosis 5 on the abdominis rectus muscle sheath 1. The M-I side will also be free and placed beneath the external oblique muscle aponeurosis 2, as shown in FIG. 5.

FIG. 5 shows the whole double layer dynamic prosthesis, according to the present invention, made of the lower prosthesic layer 9 and the upper prosthesic layer 13. The upper prosthesic layer 13 (FIG. 4) is placed over the lower prosthesis layer 9, which is shown positioned in FIG. 3, said upper prosthesic layer having its H-I side fixed to the inguinal ligament 6 with second suture stitches 12, which can be spaced out or in continuous succession.

The semilunar shaped incision 14 favours and facilitates the passage and the emergence of the spermatic cord 3. Once the external oblique muscle aponeurosis 5 is lifted, the surgeon, with a digital movement, without causing plicas and torsion, stretches the H-M side of the upper prosthesic layer 13 between the abdominis rectus muscle 1 and the external oblique muscle aponeurosis 5. The external oblique muscle aponeurosis 5 will be laid down on the whole prosthesis and sutured.

Figure 6B:
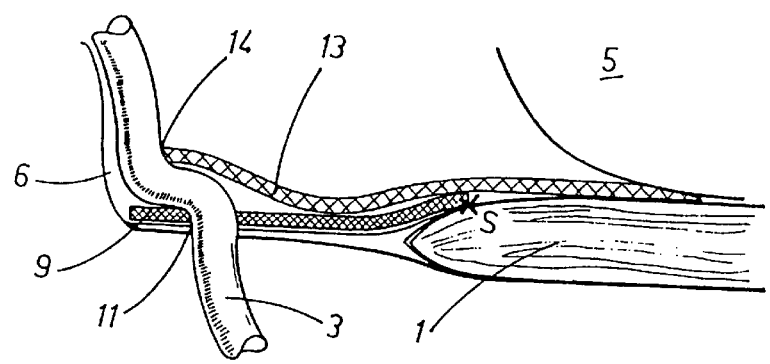
Figure 6C:
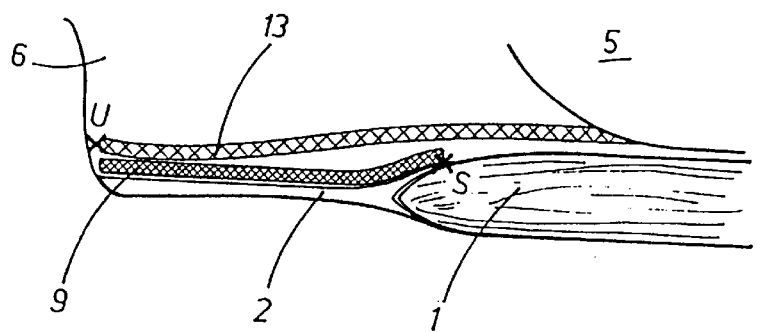

FIG. 6 shows three sections, denoted with 6.1, 6.2, and 6.3 of the inguinal region respectively passing downstream, through and upstream the internal inguinal orifice. The section shown in 6.1, passing downstream of the internal inguinal orifice, shows the external oblique muscle aponeurosis 5, the inguinal ligament 6, the trasversalis fascia 7, the small oblique and transversal muscles 2 and the abdominis rectus muscle 1.

The lower prosthetic layer 9 is sutured in the point indicated with (S) to the abdominis rectus muscle sheath 1. The upper prosthetic layer 13 is sutured in the point indicated with (U) to the inguinal ligament 6.

The section shown in 6.2, passing through the internal inguinal orifice, shows an S-shape taken up by the spermatic cord 3 that comes out to the surface by crossing the lower prosthetic layer 9 through the orifice 11, and the upper layer 13 through the semilunar incision 14.

The section shown in 6.3 shows the two prosthetic layers 9 and 13 upstream of the internal inguinal orifice both sutured at points (S) and (U), the upper layer 13 to inguinal ligament 6 and the lower 9 to the abdominis rectus muscle 1.

Advantageously, the periphery of the two lower 9 and upper 13 prosthesic layers can be reinforced with a border, denoted with 15 in FIGS. 4 and 5 with the same or different materials.

Furthermore, the two lower 9 and upper 13 prosthesic layers can be made in reabsorbable, non-reabsorbable or mixed materials. The above described invention, in addition to the characteristics already mentioned, has the following advantages:

it compels the spermatic cord 3 to follow an S-shaped route that is emphasized during a muscular effort (cough, effort, deambulation and so on), thus preventing eventual external oblique relapses from occurring;

the "sling" effect, exerted by the lower prosthesic layer 9 on the spermatic cord 3, tends to medially move the spermatic cord 3 so as to reduce the space between the cord itself and the medial margin of the internal inguinal orifice, where the external oblique relapsing hernias occur. The portion of cord situated between the internal inguinal orifice and the semilunar incision 14 of the upper prosthetic layer 13 is pressed between the floor of the inguinal canal 7, under the endoabdominal pressure, and the double prosthesic layer 9 and 13. This creates a sandwich mechanism in which the spermatic cord 3 acts as a closing and protecting element for the internal inguinal orifice;

the lower prosthetic layer 9, being only medially (A-D side) fixed, can move only in that direction. When movement occurs, the "sling" action on the spermatic cord 3 is emphasised and therefore the internal inguinal orifice is reduced;

the upper prosthesic layer 13 fixed only laterally to the inguinal ligament 6 (H-I side), can move only in that direction, therefore in an opposite direction with respect to the direction of the lower prosthetic layer 9. This involves:

a) the reciprocal independence of the prosthetic layers 9 and 13;

b) the complementary reinforcement of the floor of the inguinal canal 7;

c) the absence of tension points on both prosthetic layers 9 and 13;

d) the suitability to any shape or change of the abdominal wall tension, during a muscular effort;

e) the emphasis of the S-shaped of the spermatic cord 3;

f) the additional stabilisation exerted by the portion of the cord 3 situated between both prosthetic layers 9 and 13 which stabilisation partially fixes the side (EF) of the lower prosthetic layer 9;

g) the prevention of the lifting of the side E-F of the lower prosthetic layer 9, thanks to the spermatic cord 3 which is placed over said side E-F and thanks to the upper prosthetic layer 13 which is fixed to the inguinal ligament 6 in correspondence of its side H-I;

h) the prevention of the lifting of the medial side M-H of the upper prosthetic layer 13 since it is situated between the abdominis rectus muscle sheath 1 and the external oblique aponeurosis 5 which increase their hold during efforts;

i) the protective action exerted on the medial sector of upper prosthetic layer 13 by the lower prosthetic layer 9 medially fixed (side A-D).

The described preferred shape of the prosthetic lower 9 and upper 13 layers allows their application on the suprafascial plane, thus avoiding any contact between prosthetic material and peritoneum. Furthermore, the dynamic prosthesis according to the present invention makes it possible to have a protected area thanks to the complementary action of the two prosthetic layers 9 and 13; said area is variable in such a way as to adapt, in the best possible way, to individual anatomic variations and to the modifications occurring in the same patient in relation to the changes of decubitus and other muscular efforts.

The present invention is susceptible to numerous variations or changes without falling outside the scope of the present invention. Furthermore, all details can be replaced by technically equivalent elements.

Obviously, in actual practice, it is possible to make variations and/or improve the present invention without falling outside the field of the following claims.

I claim:

1. Double layer dynamic prosthesis for surgical treatment of inguinal hernia, made of a thin layer of prosthetic material, said prosthesis comprising:

a lower prosthetic layer and an upper prosthetic layer placed over said lower prosthetic layer, both said lower prosthetic layer and an upper prosthetic layer adapted to be independently mobile from each other and being fixed with first and second suture stitches to the musculoaponeurotic structures of the inguinal canal;

each prosthetic layer being fixed on only one side thereof, opposite to a single fixed side of the other layer;

said lower prosthetic layer and upper prosthetic layer determining between them an S-shape of the spermatic cord;

said lower prosthetic layer and upper prosthetic layer protecting the inguinal canal, in a coupled and complementary way, on a variable area so as to adapt to individual anatomic variations and modifications which occur in the patient during normal physical activity.

2. The prosthesis as in claim 1 wherein the lower prosthetic layer has a substantially trapezoidal shape and includes, starting from a first side corresponding to a medial side, an incision from the first side to an orifice for passage of the spermatic cord;

said incision defining on the first side two offshoots destined to be fixed with first suture stitches to the rectus muscle;

a second side, opposite to the first side, being shaped in such a way as to lap the inguinal ligament of the orifice without suture stitches, and intermediate sides being destined to be respectively positioned downstream and upstream of the internal inguinal orifice.

3. The prosthesis as in claim 1 wherein the upper prosthesis layer includes a first side, which is destined to be fixed with second suture stitches, said first side stretching from the tubercle of the pubis so as to overcome the internal inguinal orifice according to a suitable orientation, said first side overlapping the side of the inguinal ligaments;

a medial side, destined to remain free without suture stitches, being placed flat on the sheath of the abdominis rectus muscle and including a rounded shape corresponding to the fusion of the external oblique aponeurosis on the abdominis rectus muscle sheath; and a third side, concurrent with the first side and the medial side, being freely placed beneath the external oblique aponeurosis muscle; and wherein the upper prosthetic layer includes an overall shape which is the same as the surface defined laterally by the inguinal ligament, medially by the fusion between the external oblique aponeurosis and the abdominis rectus muscle, and beneath by the tubercle of the pubis.

4. The prosthesis as in claim 3 wherein the upper prosthetic layer includes on the first side a semilunar incision facilitating passage to the surface of the spermatic cord.

5. The prosthesis as in claim 1 wherein the periphery of the lower and upper prosthetic layers is provided with a reinforcement border.

\* \* \* \* \*